United States Patent [19]
Real et al.

[11] Patent Number: 5,583,713
[45] Date of Patent: Dec. 10, 1996

[54] PIPELINED DEMODULATION AND ADC CONVERSION SCHEME FOR DISK DRIVE SERVO SYSTEM

[75] Inventors: Peter Real; Mairtin Walsh; Kenneth Deevy; Patrick Griffin; Philip Quinlan, all of Limerick, Ireland

[73] Assignee: Analog Devices, Inc., Norwood, Mass.

[21] Appl. No.: 279,299

[22] Filed: Jul. 22, 1994

[51] Int. Cl.$^6$ .............................. G11B 5/596; G11B 5/09
[52] U.S. Cl. ............................................ 360/77.08; 360/46
[58] Field of Search .................................... 360/77.08, 46, 360/77.11, 78.06, 78.08, 78.14

[56] References Cited

U.S. PATENT DOCUMENTS 5,301,072  4/1994  Wilson .............................. 360/77.08 X Primary Examiner—W. Chris Kim
Attorney, Agent, or Firm—Wolf, Greenfield & Sacks, P.C.

[57] ABSTRACT

A servo system for controlling the position of a read/write head in a disk drive is provided. The servo system includes an input terminal for sequentially receiving a plurality of input signal bursts of a burst pattern, wherein the input signal bursts include positional information of the head. Demodulation circuitry, coupled to the input terminal, sequentially demodulates each input signal burst and provides a demodulated signal for each burst. An ADC, coupled to the demodulation circuitry, sequentially converts each demodulated signal. The ADC converts a first demodulated signal corresponding to the first of the plurality of input signal bursts before the demodulation circuitry completes demodulating the next of the plurality of input signal bursts. In a preferred embodiment, the ADC converts a demodulated signal corresponding to a first input signal burst while the demodulation circuitry demodulates a signal corresponding to a second, and subsequent, input signal burst. Thus, a pipelined demodulation and conversion scheme is disclosed in which time delays between demodulation and conversion are reduced. In the preferred embodiment, the demodulation circuitry includes area detect circuitry having an integration circuit and a single track-and-hold amplifier.

9 Claims, 4 Drawing Sheets

PIPELINED DEMODULATION AND ADC CONVERSION SCHEME FOR DISK DRIVE SERVO SYSTEM

FIELD OF THE INVENTION

The present invention relates to a servo system for controlling the position of a read/write head in a disk drive and, more particularly, to a pipelined demodulation scheme for sequentially demodulating and digitizing input signal bursts containing head positional information.

BACKGROUND OF THE INVENTION

Servo systems are commonly used in disk drives to control the position of a read/write head. Head positional information is typically contained in tracking control signals which are stored on, and read from, a disk. Servo systems include analog demodulation circuitry for demodulating the tracking control signals and conversion circuitry for digitizing the demodulated signals. Digital circuitry processes the digitized signals and calculates a digital error signal representing the physical distance and/or direction between the desired and the actual head position. The error signal is converted to an analog voltage which is used to control and correct the position of the head.

Principally two approaches have been used to provide tracking control signals indicative of position on a disk surface. In the first approach, tracking control signals are stored on a separate surface (from that on which data is stored) of a multi-surface disk. In the second approach, in an effort to save disk space, it has become increasingly common for disk manufacturers to embed short duration servo bursts (tracking control signals) in dedicated servo areas interspersed between data storage areas, both on single-surface and on multi-surface disks. Typically, a repeated pattern of several (e.g., four) servo bursts is embedded on the disk. In each pattern, the bursts are substantially arranged along a track so that the bursts will be sequentially read if the head stays on the track. Each burst in the pattern is radially offset from the track and with respect to the other bursts. The relative amplitudes of the signal bursts (or, correspondingly, the integrated values of the detected bursts) read by the head provides information from which the head position (relative to the track) can be determined and, thus, is used to generate a positional error signal.

Prior art servo systems have been developed with circuitry for demodulating and digitizing embedded servo bursts. The demodulation circuitry of such systems typically includes circuitry for sequentially determining the amplitude of (or integrated area beneath) each signal burst within a pattern. The amplitude (or, as an alternative, the area) information for each burst is stored separately in the form of a detected analog voltage (or corresponding charge). Upon demodulation of the last burst of the pattern, conversion circuitry then sequentially digitizes and stores the analog voltage for each burst for subsequent head position correction.

One such prior art servo system is shown in FIG. 1 and includes input leads 10 and 12 for respectively receiving the differential, AC-coupled, input signals $V_{IN}+$ and $V_{IN}-$ from a read head which reads, for example, four sequential burst signals A, B, C and D of a pattern. Typical signal bursts A, B and C, as read by a head, are shown in FIG. 2 (burst D is not shown). The signal bursts A, B, C and D commonly have the same frequency, which generally ranges from 3–10 MHz. The signal bursts generally have the same amplitude on the disk but the signal bursts read from the disk by the head have different amplitudes (as shown in FIG. 2) due to the radial position of the head with respect the signal bursts (which are themselves radially offset from one another). Area detect circuitry 14 separately and sequentially rectifies and integrates each burst to determine the "area" under each signal burst, and temporarily stores a voltage representing the area information. Analog-to-digital converter ("ADC") 26 then sequentially digitizes the stored voltages for the bursts A, B, C and D.

Area detect circuitry 14 includes an operational transconductance amplifier (OTA) 16, a full-wave rectifier 18, an integrator 20 and a stack 22 of four track-and-hold amplifiers (T/H) 22A–22D. As will be readily understood by those skilled in the art, the full-wave rectifier 18 rectifies the differential voltage received on leads 10 and 12 and provides the rectified voltages to OTA 16. OTA 16 then translates the rectified voltages to a driving current and that current is provided to integrator 20. Integrator 20 integrates the rectified current. Those skilled in the art will understand that integrator 20 includes a capacitor which is charged by the rectified current signal and that the accumulated charge (and corresponding voltage) represents (i.e., is proportional to) the area beneath the rectified current signal. For each burst, a voltage representing the area is thus output by the integrator. Those skilled in the art will also appreciate that peak detect circuitry could alternatively be used to demodulate the signal bursts but that area detect circuitry is more immune to noise (i.e., spikes in the signal bursts).

The output voltages of the integrator for bursts A, B, C and D are stored in the four track-and-hold amplifiers T/H 22A, T/H 22B, T/H 22C and T/H 22D, respectively. For each burst, the output voltage of the integrator is "tracked" by a capacitor in the appropriate track-and-hold amplifier and, upon completion of the integration of that burst, the instantaneous voltage is "held" by the track-and-hold amplifier capacitor to enable subsequent digitization.

Upon demodulation of each of the bursts in the pattern, ADC 26 then sequentially converts to a digital signal each held analog voltage of a T/H 22A–22D. A multiplexer (not shown) sequentially provides the analog voltage outputs of the track-and-hold amplifiers along line 24 to ADC 26 for the bursts A, B, C and D. For each signal burst, the ADC 26 outputs a digital value (at a resolution of, e.g., 10-bits) representing the area information. The digital signal outputs of the ADC for the bursts A, B, C and D are sequentially fed along lines (or bus) 28 and stored in the registers labelled 30A, 30B, 30C and 30D, respectively, of register stack 30.

Once stored, the digital information is fed along lines (bus) 32 to microprocessor 34 which calculates an error signal. The error signal is provided on lines (bus) 36 to digital-to-analog converter ("DAC") 38. The DAC 38 provides an analog output signal along line 40 to DAC output amplifier 42 which, in turn, provides an output signal on line 44 to control and correct the head position (i.e., via a motor, not shown).

In such a prior art system, a delay occurs between the demodulation of each signal burst and the conversion of the demodulated signal burst. The delay occurs because a demodulated burst, burst A, for example, is not digitized until after each of the other bursts, bursts B, C and D in this example, has been demodulated. As a result of the delay, the read/write head may experience some wiggling movement. Additionally, the delay in conversion causes a delay in the positional correction of the head. Such effects may, in turn, cause faulty or inaccurate disk drive operation.

SUMMARY OF THE INVENTION

According to the present invention, a pipelined demodulation scheme is provided for use in a disk drive head-positioning servo to sequentially demodulate each of a plurality of servo signal bursts in a pattern, and to sequentially digitize each demodulated burst with minimal delay between the demodulation and digitizing of each servo signal burst.

More particularly, in a servo system employing the present invention, there is an input which sequentially receives a plurality of input servo signal bursts of a burst pattern. Demodulation circuitry, coupled to the input, sequentially demodulates each input signal burst and provides an analog demodulated signal for each burst. An ADC is coupled to the demodulation circuitry and sequentially converts each analog demodulated signal to a digital output signal. The ADC converts a first demodulated signal corresponding to a first of the plurality of input signal bursts before the demodulation circuitry completes demodulating a second of the plurality of input signal bursts.

In a preferred embodiment of the present invention, the demodulation circuitry includes area detect circuitry. The area detect circuitry includes an integrator, coupled to the input terminal, for integrating each input signal burst and providing an integrated output voltage, and a track-and-hold amplifier, coupled to the integrator output, for providing a held output voltage corresponding to an integrated output voltage for each burst.

In a preferred embodiment of the present invention, the ADC converts a held output voltage corresponding to a first input signal burst while the integrator integrates a signal corresponding to a second, and subsequent, input signal burst.

DETAILED DESCRIPTION

Figure 1:
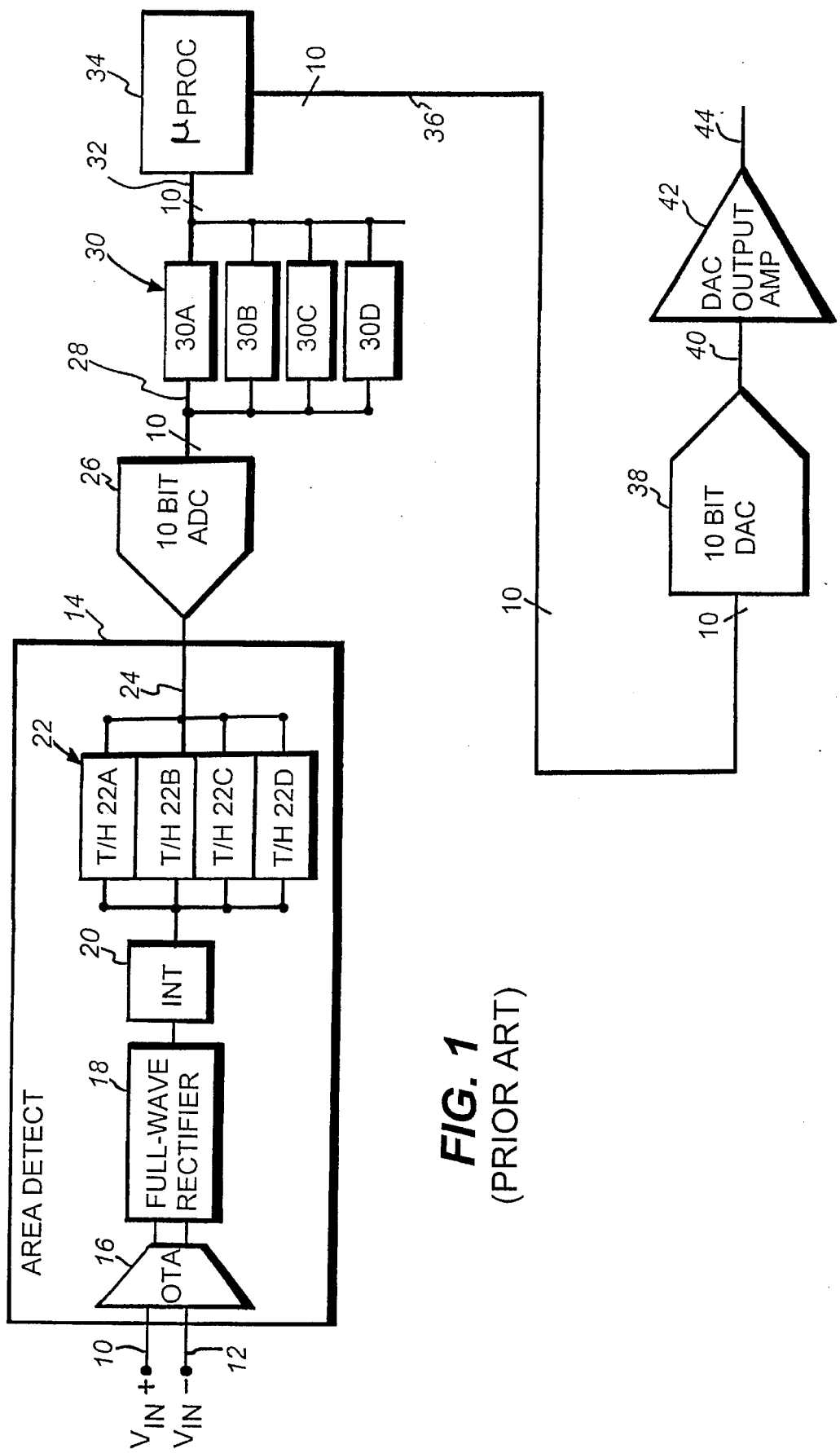
FIG. 1 is a block diagram of a prior art servo system.
Figure 2:
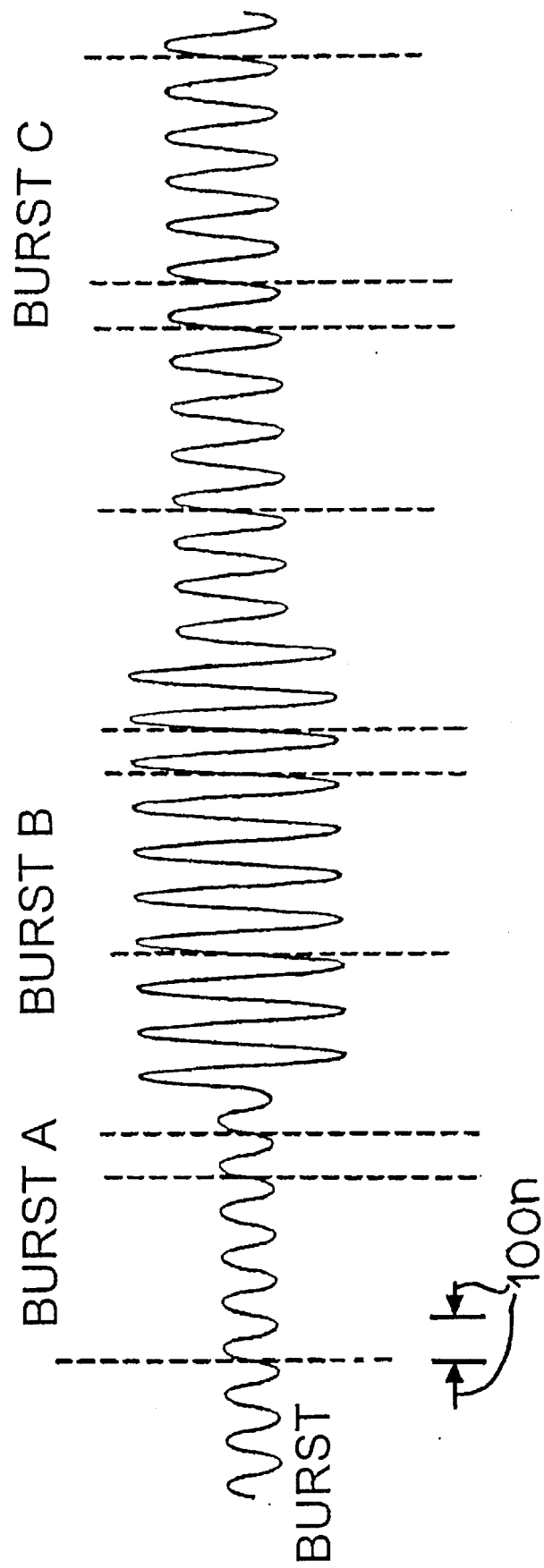
FIG. 2 is a timing diagram of typical burst signals read from a disk.

By contrast with prior art servo systems, the system of the present invention includes a pipelined demodulation scheme in which there is minimal delay between demodulation and conversion of each servo burst. Specifically, referring to FIG. 3 (where like elements are referred to by identical reference characters to those in FIG. 1), the servo system of the present invention includes area detect circuitry 15 and an ADC 26. During operation, the area detect circuitry 15 demodulates a first signal burst A of a pattern of bursts such as A, B, C and D (shown in the timing diagram of FIG. 4). Then, the ADC 26 digitizes the demodulated signal burst A while the area detect circuitry is demodulating the next sequential signal burst B. Such a demodulation and conversion routine continues until each signal burst A, B, C and D has been demodulated and digitized.

Figure 3:
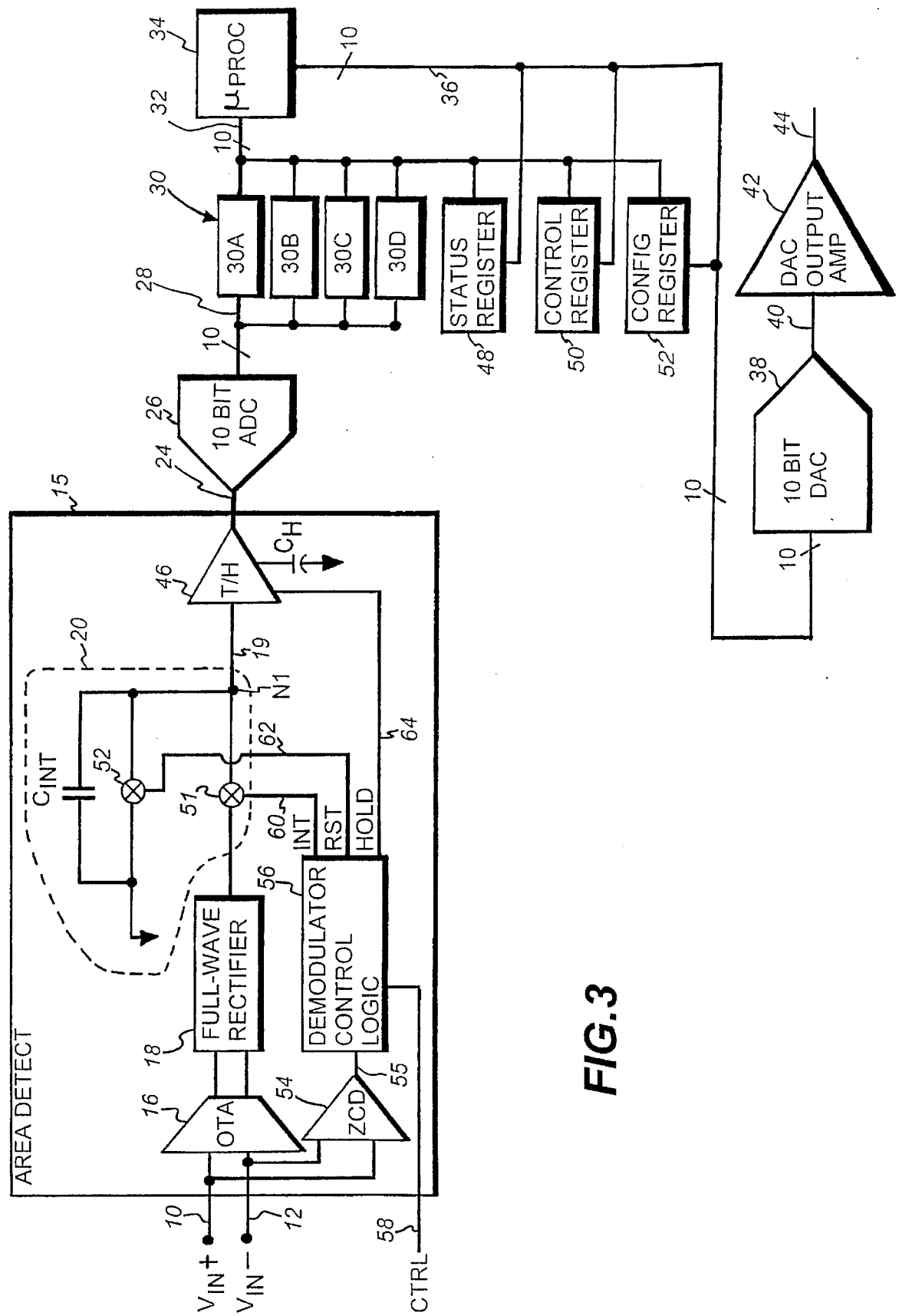
FIG. 3 is a partial schematic, partial block diagram of a servo system embodying the present invention.
Figure 4:
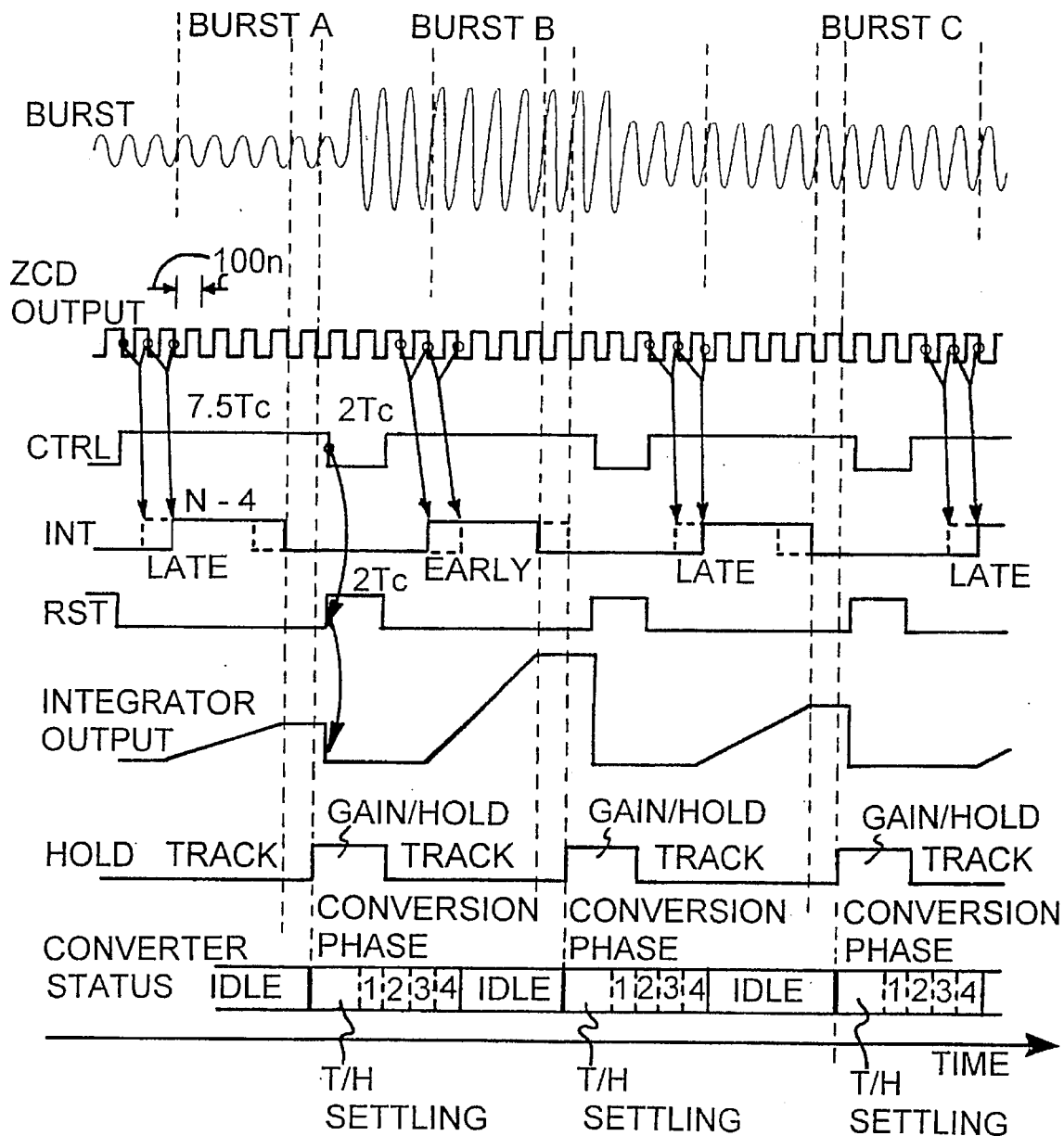
FIG. 4 is a timing diagram of various signals of the servo system of FIG. 3.

FIG. 4 is a timing diagram showing various signals associated with the servo system of FIG. 3. The signals are shown on the same time axis and the physical placement of one signal above another does not signify that one attains a higher voltage level than another. Three signal bursts A, B and C are shown in FIG. 4. Typically, four signal bursts are provided. Burst D is not shown, however, because the pipelined demodulation and conversion scheme can be readily understood by examining operation of the servo system on bursts A, B and C. As shown in FIG. 4, the bursts have the same frequency but different amplitudes.

The system of the present invention, like the prior art system of FIG. 1, includes differential input leads 10 and 12 respectively receiving from the head the AC-coupled input voltages $V_{IN}+$ and $V_{IN}-$ of input signal bursts A, B, C and D. Area detect circuitry 15 determines the area beneath each rectified signal burst A, B, C and D and provides an analog voltage signal, corresponding to the area, on line 24 to ADC 26. ADC 26 converts each analog signal to a digital signal (of, e.g., 10-bit resolution), which is provided on lines (bus) 28 to register stack 30, including registers 30A, 30B, 30C and 30D. Registers 30A, 30B, 30C and 30D respectively store the digitized area signals for bursts A, B, C and D. Microprocessor 34 receives the digitized area signals from register stack 30 on lines (bus) 32 and generates a digital position error signal.

As in the prior art system of FIG. 1, the microprocessor 34 provides the digital error signal on lines (bus) 36 to DAC 38 which, in turn, converts the digital error signal to an analog error voltage. The analog voltage is provided on line 40 to DAC output amplifier 42 which, in turn, provides an output signal on line 44 to control and correct the head position.

Like the prior art servo system, the area detect circuitry 15 of the servo system of the present invention includes an OTA 16 connected to the input leads 10 and 12, a full-wave rectifier 18 connected to the differential outputs of the OTA, and an integrator 20 connected to the output of the full-wave rectifier. The OTA 16, for each signal burst, translates the AC-coupled differential input voltage to a differential current. The full-wave rectifier 18 rectifies the differential current and outputs a rectified current signal. Integrator 20 generates a voltage representing the area beneath the rectified current signal. Track and hold amplifier 46 sequentially tracks and holds the area voltage generated by integrator 20 for each signal burst. The voltage held by track-and-hold amplifier 46 for each signal burst is then provided along line 24 to ADC 26 where it is subsequently converted to a digital signal (at a resolution of, e.g., 10-bits). Unlike the prior art system which included four track-and-hold amplifiers for simultaneously holding the voltages corresponding to the demodulated bursts before conversion of any of the voltages, the system of the present invention includes only one track-and-hold amplifier, and conversion of each demodulated burst occurs almost immediately after demodulation of that burst. By "demodulation" of a burst, we mean that the burst is received and a signal or voltage is generated which is proportional to the burst, prior to conversion. While the demodulation scheme described includes translation to a current, rectification and integration, other demodulation schemes could be used.

As shown in detail in FIG. 3, integrator 20 includes a first switch S1 connected in the output line 19 from full-wave rectifier 18. An integrating capacitor $C_{INT}$ is connected between switch S1 and ground, with the first plate of capacitor $C_{INT}$ connected to switch S1 and the second plate of capacitor $C_{INT}$ connected to ground. A second switch S2 is connected between the first plate of capacitor $C_{INT}$ and ground. The operation of switches S1 and S2 are controlled by the control signals INT and RST, respectively. Signals INT and RST are provided to switches S1 and S2 along lines 60 and 62, respectively.

As will be appreciated by those skilled in the art, when switch S1 is closed, the integrator is "on" and when switch S1 is opened, the integrator is "off". Switch S1 is closed when signal INT is high and is opened when signal INT is low. When switch S1 is closed and switch S2 is opened, the output current from full-wave rectifier 18 will flow through switch S1 and through integrating capacitor $C_{INT}$ to ground. Such action charges capacitor $C_{INT}$. The charge accumulated on capacitor $C_{INT}$ corresponds to a voltage level representing the area beneath the current signal. Node $N_1$ will be at that voltage level (i.e., the output voltage of the integrator). When switch S1 is opened, the current is prevented from flowing through capacitor $C_{INT}$. When switch S2 is closed, the charge on capacitor $C_{INT}$ is discharged to ground, to "reset" the integrator. Switch S2 is closed when signal RST is high and is opened when signal RST is low.

Track-and-hold amplifier 46 operates to "hold" the analog output voltage of the integrator, enabling the ADC to digitize that voltage. Track-and-hold amplifier (THA) 46 typically includes a capacitor $C_H$ connected between an internal node (not shown) and ground. As will be understood by those skilled in the art, the track-and-hold amplifier can operate in a "track" mode, during which the capacitor $C_H$ is charged by the input voltage received on line 19 (and node $N_1$) and the output of the THA follows its input, and a "hold" mode, during which the present charge on capacitor $C_H$ is maintained. The voltage on output line 24 corresponds to the charge maintained on capacitor $C_H$. The operating modes of the track-and-hold amplifier 46 are controlled by signal HOLD received on line 64.

Those skilled in the art will readily understand that information relating to the input signal bursts such as the number of bursts, the frequency of the bursts, and the number of cycles over which the area detect circuitry should integrate for each burst are design parameters provided by a user. Such parameters can be fixed or programmed. The control register 50 stores a word, certain bits of which determine the number of cycles over which the integrator 20 should integrate for each burst. The status register 48 stores a word, certain bits of which determine whether the integrator has integrated correctly for each of the bursts. Thus, when the user provides the above information, a digital word representing the number of cycles over which the system should integrate is stored in the status register.

The user also provides signal CTRL (see FIG. 3) along line 58 to the demodulator control logic 56 which, in cooperation with the zero-crossing detector (ZCD) 54, insures that the correct number of complete cycles of the bursts are demodulated and integrated. Signal CTRL is a periodic signal, that is high (at a voltage level recognized as "high") once during each signal burst for a certain number of cycles. For example, as shown in FIG. 3, the signal CTRL is high for 7.5 cycles of each burst and is low for two cycles of each burst. Once during each signal burst, while the signal CTRL is high, the integrator can then perform the integration (as described above).

The ZCD 54 is connected to the differential input leads 10 and 12 and receives the AC-coupled input voltages $V_{IN}+$ and $V_{IN}-$, respectively. The ZCD 54 produces a continuous pulse stream output (see FIG. 3) along line 55 to the demodulator control logic 56. The ZCD output is a periodic signal (when the burst information is presented periodically) including a falling edge each time the differential input signal crosses through zero volts. The ZCD output signal is used by the demodulator control logic 56 to generate the control signals INT and RST for controlling operation of the integrator. As described above, the integrator only integrates when signal INT is high and the integrating capacitor discharges (the integrator is reset) when signal RST is high. The specific implementations of the OTA, the ZCD, the rectifier and the integrator are conventional and are not part of the present invention.

The timing diagram of FIG. 4 shows the signals of the servo system for the example in which the user has programmed four cycles over which the integrator should integrate for each signal burst. When signal CTRL goes high during burst A, the demodulator control logic then counts two falling edges of the ZCD output before making signal INT high to begin integration of the burst. The demodulator control logic makes signal INT high upon the second falling edge of the ZCD output to insure that the ZCD output is valid and that the integrator starts integrating at a full cycle of the input signal burst. The demodulator control logic then counts four cycles (from falling edge to falling edge) of the ZCD output and makes signal INT low on the fourth falling edge to terminate the integration of the burst after the pre-programmed number of cycles.

The asynchronous nature of signal CTRL and the ZCD output signal results in a range within which signal INT is made to go high, the range varying from one cycle to two cycles after each signal CTRL rising edge. Such a range is shown in the timing diagram of FIG. 4. As shown during burst A, the ZCD output falling edge occurs just before signal CTRL goes high. Therefore, the demodulator control logic counts two more subsequent falling edges of the ZCD output before making signal INT high. Such an occurrence is shown during burst A and is labeled "late" beneath signal INT. Alternatively, as shown during burst B, signal CTRL may go high just prior to the falling edge of the ZCD output. Therefore, that falling edge will be counted and signal INT will be made high on the subsequent falling edge of the ZCD output. Such an occurrence is shown during burst B and is labeled "early" beneath signal INT.

Shown also is signal HOLD generated by the demodulator control logic 56 and provided along line 64 to track-and-hold amplifier 46. When signal HOLD is low, the track-and-hold amplifier 46 is in track mode, and when signal HOLD is high, the track-and-hold amplifier 46 is in hold mode (as described above). Signal HOLD is low while signal INT is high (during integration) and signal HOLD goes high one full cycle after signal INT goes low causing the integrator output voltage to be held by the track-and-hold amplifier 46. (As described above, the track-and-hold amplifier holds the voltage by charging the capacitor $C_H$ to an equal or proportional charge to that on the integrating capacitor $C_{INT}$.) To insure that the track-and-hold amplifier correctly acquires an equal or proportional charge on its capacitor $C_H$ to the integrated charge, the demodulator control logic waits one full cycle of the ZCD output (i.e., one full cycle of the input burst) after signal INT goes low before signal HOLD is made high. In addition, after signal HOLD goes high, a further minimum of one half-cycle of the ZCD output occurs before signal CTRL goes low. This delay occurs so that the voltage is adequately held by the track-and-hold amplifier 46 prior to the discharging of the charge on the integrating capacitor $C_{INT}$.

For each burst, once the area voltage is held by the track-and-hold amplifier 46, that voltage is converted by the ADC 26 and the digital output signal is stored in the appropriate register 30A–30D of the register stack 30. After signal HOLD goes high, the ADC 26 waits a short period of time for the track-and-hold amplifier to settle before beginning conversion. The conversion process continues after signal HOLD goes low. As will be understood by those skilled in the art, a typical multi-bit conversion occurs in separate phases, each phase for converting a different group of bits.

As seen in the timing diagram of FIG. 4, the ADC 26 converts the voltage output by track-and-hold amplifier 46 corresponding to burst A while the integrator is integrating the rectified current corresponding to burst B. Similarly, the voltage corresponding to burst B is converted by the ADC while the integrator 20 is integrating the rectified current corresponding to burst C. Such a process of integrating a first burst and then converting that burst while integrating a subsequent burst, is referred to herein as a "pipelined" demodulation and conversion scheme. The pipelined demodulation and conversion scheme offers the advantage that the delay between integration and conversion is minimized such that the head position correction occurs quickly; that is, the servo bandwidth is higher and settling time is shorter.

After conversion of each burst, the status register stores a word, certain bits of which determine whether an accurate demodulation and conversion has occurred. If an inaccurate demodulation and conversion has occurred for any of the bursts, the process can be repeated.

It should be understood while that the example shown and described above included four input signal bursts and the number of cycles over which the integrator should integrate was four, such parameters are provided by the user and could be changed without altering the pipelined demodulation and conversion scheme of the present invention.

In addition, while the ADC, DAC and registers were shown and described herein as 10-bit converters and registers, and the lines interconnecting such elements were 10-bit buses, those skilled in the art should appreciate that different length converters and registers are suitable.

While there have been shown and described what are at present considered the preferred embodiments of the present invention, which have been disclosed by way of example only, it should be obvious to those skilled in the art that various changes and modifications can be made therein without departing from the spirit and scope of the invention as presented above and as defined by the appended claims and equivalents thereto. For example, the timing relationship between signal CTRL, signal INT and the ZCD output signal could be changed so long as the integrator 20 accurately integrates over the correct number of pre-programmed cycles. Similarly, the timing relationship between the start of the HOLD cycle and the analog-to-digital conversion process could be altered to suit a particular application. Further, while the input was shown and described in a differential arrangement, those skilled in the art will appreciate that a single-ended input could be used. Those skilled in the art should also appreciate that it is not necessary, with the scheme of the present invention, to integrate over an integer number (or a fraction such as ½) of cycles of the input burst.

What is claimed is:

1. A system for demodulating and converting a plurality of input signal bursts of a burst pattern comprising:

an input sequentially receiving the plurality of input signal bursts, wherein the demodulation circuitry includes only a single integrator, coupled to the input, that integrates each input signal burst and provides an integrated output voltage for each input signal burst;

demodulation circuitry, coupled to the input, for sequentially demodulating each input signal burst and providing a demodulated signal for each input signal burst; and an ADC, coupled to the demodulation circuitry, for sequentially converting each demodulated signal to a digital output signal;

wherein the ADC converts a first demodulated signal corresponding to a first of the plurality of input signal bursts before the demodulation circuitry completes demodulating a second of the plurality of input signal bursts.

2. A system as claimed in claim 1, wherein the demodulation circuitry further includes a track-and-hold amplifier, coupled between the integrator and the ADC, that provides a held output voltage corresponding to each integrated output voltage.

3. A system as claimed in claim 2, wherein the ADC converts a held output voltage provided by the track-and-hold amplifier corresponding to an input signal burst while the integrator integrates a signal corresponding to a subsequent input signal burst.

4. A system as claimed in claim 3, wherein the pattern of input signal bursts includes four input signal bursts.

5. A system for demodulating and converting a plurality of input signal bursts of a burst pattern comprising:

an input sequentially receiving a plurality of input signal bursts of a burst pattern;

demodulation circuitry means, coupled to the input terminal means, for sequentially demodulating each input signal burst and providing a demodulated signal for each input signal burst, wherein the demodulation circuitry means includes only a single integrator, coupled to the input, that integrates each input signal burst and provides an integrated output voltage for each input signal burst; and conversion means, coupled to the demodulation circuitry means, for sequentially converting each demodulated signal;

wherein the conversion means converts a first demodulated signal corresponding to a first-received input signal burst of the pattern of input signal bursts before the demodulation circuitry means completes demodulating a next-received input signal burst of the pattern of input signal bursts.

6. A system as claimed in claim 5, wherein the demodulation circuitry further includes a single track-and-hold amplifier, coupled to the integrator, that provides a held output voltage corresponding to each integrated output voltage.

7. A servo system as claimed in claim 6, wherein the conversion means converts a held output voltage provided by the track-and-hold amplifier corresponding to an input signal burst while the integrator integrates a signal corresponding to a subsequent input signal burst.

8. A system as claimed in claim 7, wherein the plurality of input signal bursts includes four input signal bursts.

9. A method for demodulating and converting a plurality of input signal bursts of a burst pattern comprising the steps of:

receiving a plurality of input signal bursts of a burst pattern;

using only a single integrator, sequentially demodulating each signal burst and providing a demodulated signal for each of the plurality of signal bursts; and sequentially converting each demodulated signal to a digital output signal;

wherein the step of sequentially converting includes converting a first demodulated signal corresponding to a first-received input signal burst of the plurality of input signal bursts before completing demodulation of a next-received input signal burst of the plurality of input signal bursts.

\* \* \* \* \*